(12) United States Patent
Childers

(10) Patent No.: US 10,175,103 B2
(45) Date of Patent: Jan. 8, 2019

(54) METHOD AND SYSTEM FOR MONITORING ULTRAVIOLET LIGHT FOR A FIBER CURE SYSTEM

(71) Applicant: Phoseon Technology, Inc., Hillsboro, OR (US)

(72) Inventor: Doug Childers, Portland, OR (US)

(73) Assignee: Phoseon Technology, Inc., Hillsboro, OR (US)

( * ) Notice: Subject to any disclaimer, the term of this patent is extended or adjusted under 35 U.S.C. 154(b) by 0 days.

(21) Appl. No.: 14/880,436

(22) Filed: Oct. 12, 2015

(65) Prior Publication Data

US 2016/0033326 A1 Feb. 4, 2016

Related U.S. Application Data

(63) Continuation of application No. 13/888,007, filed on May 6, 2013, now Pat. No. 9,442,007.

(51) Int. Cl.
| | | |
|---|---|---|
| *H05B 31/00* | (2006.01) | |
| *H05B 33/00* | (2006.01) | |
| *G01J 1/42* | (2006.01) | |
| *C03C 25/12* | (2006.01) | |
| *G01N 21/27* | (2006.01) | |
| *G01N 21/88* | (2006.01) | |
| *G01N 21/952* | (2006.01) | |

(Continued)

(52) U.S. Cl.
CPC .............. *G01J 1/429* (2013.01); *C03C 25/12* (2013.01); *G01N 21/274* (2013.01); *G01N 21/8806* (2013.01); *G01N 21/952* (2013.01); *B05D 3/067* (2013.01); *B05D 2256/00* (2013.01); *G01N 2021/8416* (2013.01); *G01N 2201/062* (2013.01); *G01N 2201/0637* (2013.01)

(58) Field of Classification Search
CPC . H05B 6/64; H05B 6/66; H05B 31/00; H05B 31/0018; H05B 31/0081; H05B 33/00; H05B 33/0833
USPC ........ 219/641, 642; 118/482, 490, 494, 220; 65/432, 435
See application file for complete search history.

(56) References Cited

U.S. PATENT DOCUMENTS 5,294,260 A * 3/1994 Larsen-Moss ......... B01J 19/123
118/420
5,418,369 A * 5/1995 Moore ................... B01J 19/123
250/372

(Continued)

FOREIGN PATENT DOCUMENTS

| CN | 102336530 A | 2/2012 |
|---|---|---|
| JP | H0255248 A | 2/1990 |

(Continued)

OTHER PUBLICATIONS

ISA Korean Intellectual Property Office, International Search Report and Written Opinion Issued in Application No. PCT/US2014/035005, dated Aug. 26, 2014, WIPO, 9 pages.

(Continued)

*Primary Examiner* — Michael Laflame, Jr.
(74) *Attorney, Agent, or Firm* — McCoy Russell LLP

(57) ABSTRACT

A system and method for monitoring and operating one or more light emitting devices is disclosed. In one example, light intensity within a dual elliptical reflecting chamber is sensed and operation of a fiber curing system is adjusted in response to an amount of sensed light energy.

14 Claims, 6 Drawing Sheets

(51) Int. Cl.
*B05D 3/06* (2006.01)
*G01N 21/84* (2006.01)

(56) References Cited

U.S. PATENT DOCUMENTS

| | | | | |
|---|---|---|---|---|
| 6,345,149 | B1* | 2/2002 | Ervin | B01J 19/123 |
| | | | | 118/641 |
| 6,502,429 | B1* | 1/2003 | Abe | C03B 37/0253 |
| | | | | 65/377 |
| 6,626,561 | B2* | 9/2003 | Carter | F26B 3/28 |
| | | | | 250/455.11 |
| 8,274,649 | B2* | 9/2012 | Hamilton, II | G01J 1/4228 |
| | | | | 315/291 |
| 2003/0026919 | A1* | 2/2003 | Kojima | C03C 25/12 |
| | | | | 427/558 |
| 2004/0017558 | A1* | 1/2004 | Lee | C03B 37/0253 |
| | | | | 356/73.1 |
| 2004/0026400 | A1* | 2/2004 | Ptak | C23C 16/481 |
| | | | | 219/390 |
| 2004/0067037 | A1 | 4/2004 | Tausch et al. | |
| 2006/0249078 | A1 | 11/2006 | Nowak et al. | |
| 2012/0009358 | A1* | 1/2012 | Gharbi | C03C 25/12 |
| | | | | 427/595 |
| 2013/0068969 | A1 | 3/2013 | Childers | |
| 2013/0092847 | A1 | 4/2013 | Childers | |

FOREIGN PATENT DOCUMENTS

| | | |
|---|---|---|
| JP | H0891878 A | 4/1996 |
| JP | H11142238 A | 5/1999 |
| JP | H11302041 A | 11/1999 |
| JP | 2002356344 A | 12/2002 |
| JP | 2003131090 A | 5/2003 |

OTHER PUBLICATIONS

State Intellectual Property Office of the People's Republic of China, Office Action and Search Report Issued in Application No. 201480026008.3, dated Jun. 1, 2017, 20 pages. (Submitted with Partial Translation).

Japanese Patent Office, Office Action Issued in Application No. 2016512912, dated Mar. 20, 2018, 9 pages.

* cited by examiner

METHOD AND SYSTEM FOR MONITORING ULTRAVIOLET LIGHT FOR A FIBER CURE SYSTEM

CROSS REFERENCE TO RELATED APPLICATIONS

The present application is a continuation of U.S. Non-Provisional application Ser. No. 13/888,007, entitled "METHOD AND SYSTEM FOR MONITORING ULTRAVIOLET LIGHT FOR A FIBER CURE SYSTEM," and filed on May 6, 2013, the entire contents of which are hereby incorporated by reference for all purposes.

BACKGROUND/SUMMARY

Optical fibers may be used to transfer light from an emitting source to a receiver. The light source may transmit data within emitted light to support communication between two ends of the optical fibers. The optical fibers may be protected from scratches and abrasions by a coating that covers the optical fiber's length. The protective coating may be cured via exposing it to a certain wavelength of light energy. In one example, the coating cures when it is exposed to ultraviolet (UV) light. The amount of time to cure the coating may depend on the light intensity and the amount of time the coating is exposed to the light. If light intensity provided to the optical fiber and its coating is greater than a desired light intensity, excess power may be consumed by the lighting system and lighting system cooling may not be sufficient to cool the light source. If light intensity provided to the optical fiber and its coating is less than a desired light intensity, the optical fiber coating may not cure as desired.

One system for curing optical fiber coatings is described in U.S. Pat. No. 5,418,369. An elliptical reflecting chamber, a UV light bulb, and two UV sensing devices placed outside the elliptical reflecting chamber. The first UV sensor monitors an amount of light emitted from the UV bulb, the second UV sensor monitors light passing through a curing tube and an average of light eluding the curing tube is described. However, the elliptical reflecting chamber and light bulb described in U.S. Pat. No. 5,418,369 may not be as efficient as is desired and some of the light exiting the elliptical reflecting chamber may not reach the UV sensor because the UV sensor is positioned away from the elliptical reflecting chamber.

The inventor herein has recognized the above-mentioned issues and has developed a system for monitoring fiber curing. In one example, a system and method for monitoring and operating one or more light emitting devices is disclosed. In one example, light intensity within a dual elliptical reflecting chamber is sensed and operation of a fiber curing system is adjusted in response to an amount of sensed light energy.

The system may comprise an elliptical reflecting chamber including at least one light emitting device directed at a curing tube and corresponding sensing port; two light sources, the curing tube positioned within at least a portion of the elliptical reflecting chamber; and a light receiver in optical communication with the light sensing port. Further, in some examples, at least two light emitting devices, each with a corresponding port, may be used. In such an example, by sensing light from two light sources that direct light at a curing tube within an elliptical reflection chamber, it may be possible to combine light energy from two or more locations around the periphery of the elliptical reflection chamber to determine an average amount of light energy directed at the curing tube. Further, the two light sensing ports may receive optical fibers that start flush with the elliptical chamber wall so that light that encounters the optical fiber is sensed rather than being able to exit the elliptical chamber without reaching a photodetector. In this way, a light receiver may not have to be within an unobstructed line of sight to the light source. Further, the elliptical reflection chamber may be formed such that all sides of a fiber being cured receive similar amounts of light energy so that the fiber cures more evenly and so that the curing system uses less energy to cure a coating applied to the fiber.

The present description may provide several advantages. In particular, the approach may provide an improved estimate of average light energy supplied to a fiber curing chamber. Additionally, the approach may be useful for controlling fiber curing system operation and indicating whether or not light source degradation is present. Further, the approach may also provide light energy monitoring for a more energy efficient fiber curing system.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE FIGURES

FIGS. 3A, 3B, and 4 are shown approximately to scale.

DETAILED DESCRIPTION

Figure 1:
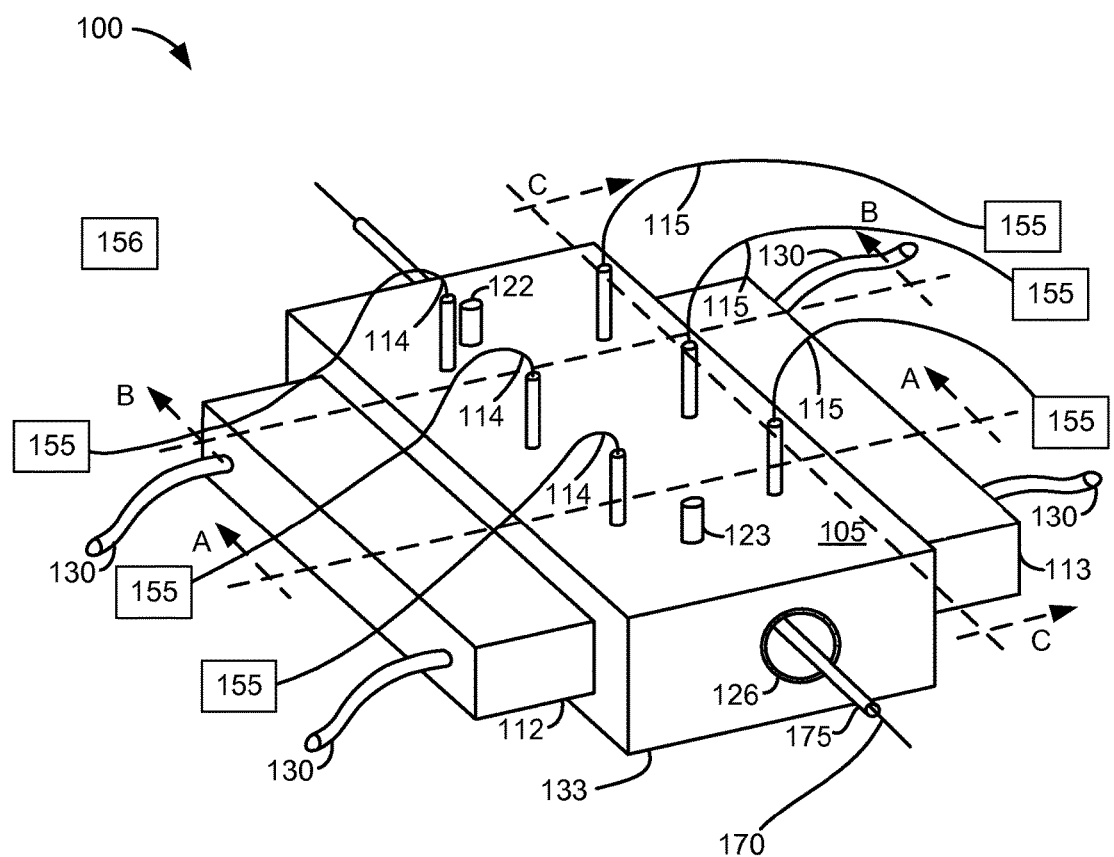
FIG. 1 shows a schematic depiction of a fiber curing system.
Figure 2:
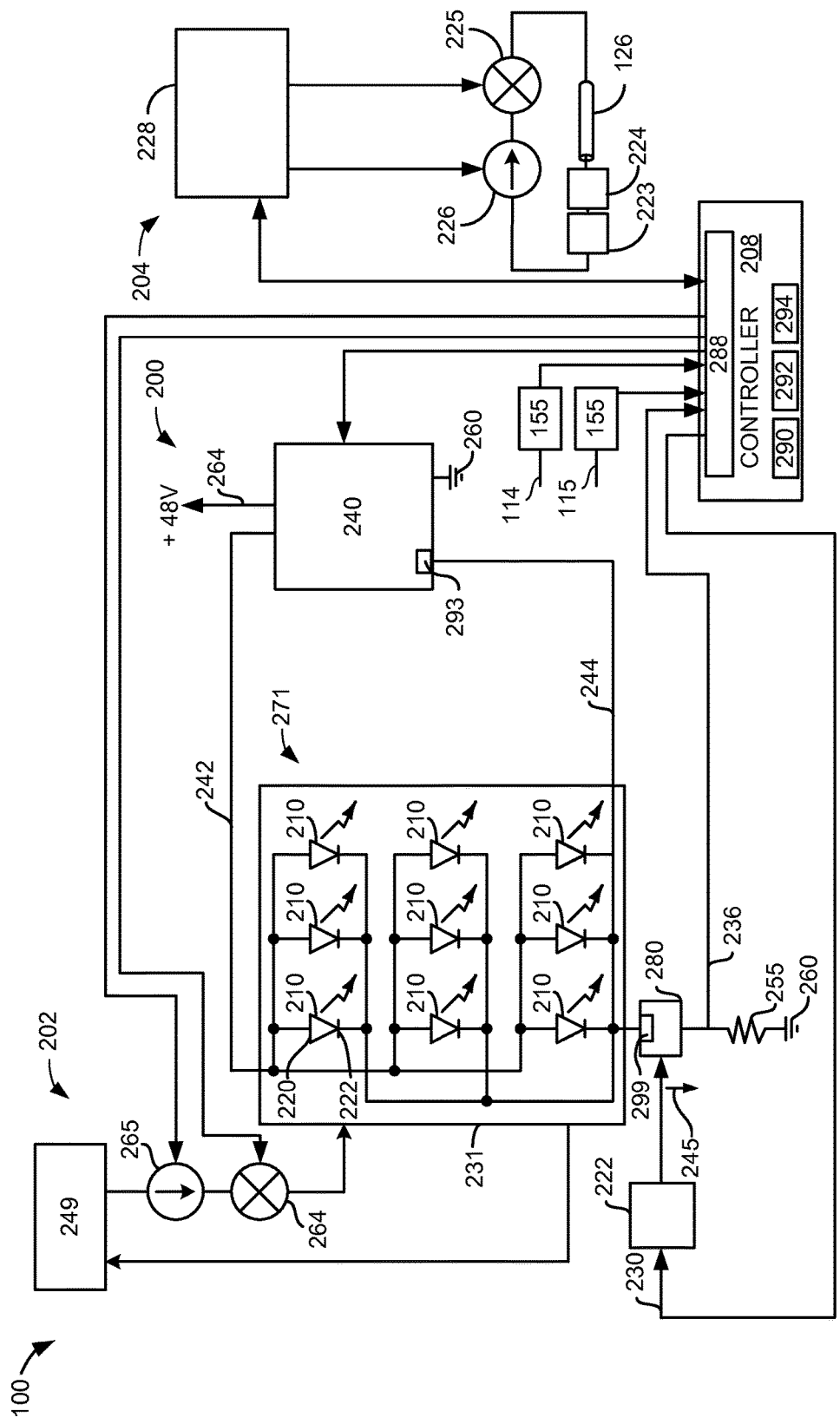
FIG. 2 shows a schematic of example fiber curing system subsystems.
Figure 3A:
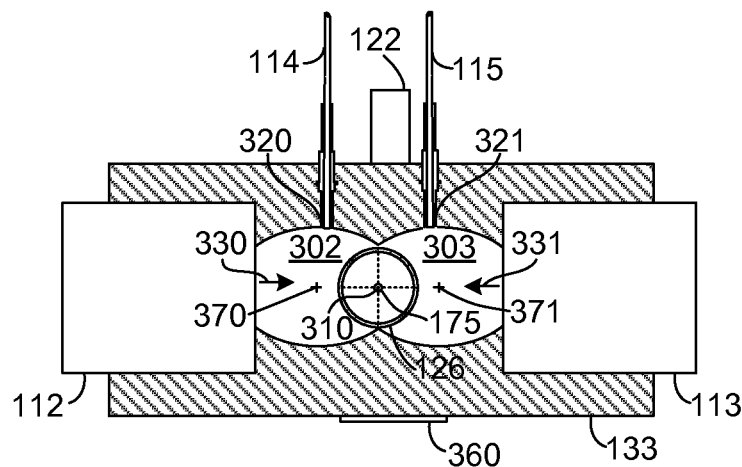
FIG. 3A shows an example cross section of a fiber curing system illustrating light energy sensing ports.
Figure 3B:
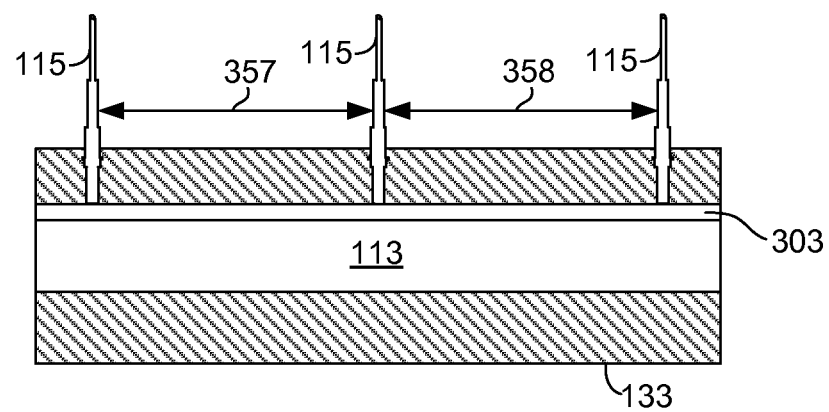
FIG. 3B shows an example longitudinal cross section of a fiber curing system illustrating light energy sensing ports.
Figure 4:
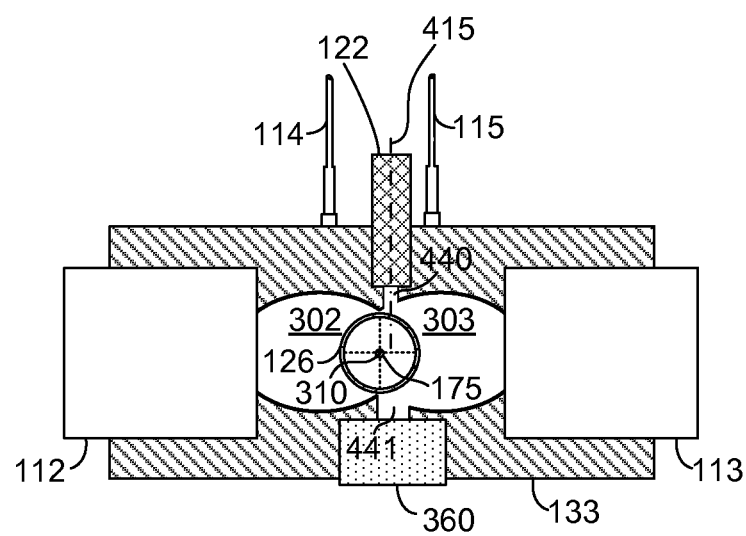
FIG. 4 shows an example cross section of a fiber curing system illustrating curing tube clarity determining devices.

The present description is related to a fiber curing system for curing a coating that is applied to a fiber. FIG. 1 shows one example fiber curing system which includes an elliptical reflecting chamber that concentrates light toward a coated fiber. Energy from light supplied into the elliptical reflecting chamber acts to cure the coating that is applied to the fiber. The fiber curing system may include subsystems as shown in FIG. 2. Light energy within the elliptical reflecting chamber may be sensed via light sensing ports as shown in FIG. 3. Clarity and/or transmittance of a curing tube within the fiber curing system may be determined via devices as shown in FIG. 4. A method for determining an amount of light energy output from a fiber curing system is described in FIG. 5. Finally, a method for determining clarity or transmittance of a curing tube is described in FIG. 6.

Referring now to FIG. 1, a schematic depiction of a fiber curing system is shown. In this example, the fiber curing system is for curing a fiber protecting coating that is applied to a single fiber. However, in other examples, the fiber curing system may be in a form that cures a coating that is applied to a plurality of fibers arranged in a ribbon. Additionally, the systems and methods described herein may be applicable to fiber curing systems having other arrangements.

A fiber 175 coated with a liquid is drawn through body 133 and curing tube 126 when fiber curing system 100 is operating. Curing tube 126 may be formed of quartz glass or another material that allows light to pass through curing tube 126. Light energy is directed at fiber 175 within an elliptical reflecting chamber (not shown) in body 133. The light energy cures the protective coating and a solid protective layer is formed over fiber 175. During the curing process, vapors may be emitted from the protective coating as it cures. The vapor may deposit on the inside of curing tube 126, thereby reducing the transmittance of curing tube 126 and decreasing the efficiency of fiber curing system 100. Inert gas, such as nitrogen ($N_2$), may flow through curing tube 126 to purge vapors from curing tube 126. However, deposits may form on curing tube 126 even though inert gas is flowing through curing tube 126.

Fiber curing system 100 includes a body 133 which includes elliptical reflecting chambers (not shown). Body 133 may be comprised of several sections that are coupled together. At least one light emitting source may be used, including one or more of light sources 112 and 113. Additionally, at least two light emitting sources may be used.

First light source 112 and second light source 113 are coupled to body 133 and arranged longitudinally with long axis 170. First light source 112 directs light into body 133 and in a direction of second light source 113. Likewise, second light source 113 directs light into body 133 and in a direction of first light source 112. Thus, both first light source 112 and second light source 113 direct light energy toward curing tube 126. First light source 112 and second light source 113 may be cooled via a liquid coolant supplied from a chiller (not shown) via coolant lines 130. A third light source 122 and a fourth light source 123 supply light that is used to determine the clarity and/or transmittance of curing tube 126. Light detectors or receivers are positioned on a side of body 133 opposite side 105 to receive light from third light source 122 and fourth light source 123. It should be noted that although the present example includes two light sources and receivers for determining clarity and/or transmittance of curing tube 126, other example may include from 1 to N light sources and receivers for determining clarity and/or transmittance of curing tube 126. Optical fibers 114 and 115 are also coupled to body 133.

First light source 112 and second light source 113 may include a plurality of light emitting arrays. In one example, each light emitting array includes a plurality of light emitting diodes (LEDs). The light emitting arrays may be arranged in a column along long axis 170. For example, first light source 112 and second light source 113 may include three light emitting arrays arranged in a single column that includes three rows, the column formed in the direction of long axis 170. In other examples, the first 112 and second 113 light source may be configured with different numbers of rows and columns of light emitting arrays. The light emitting arrays direct light energy toward fiber 175 inside of body 133.

Left side optical fibers 114 and right side optical fibers 115 transmit light energy output from first light source 112 and second light source 113 to a plurality of photodetectors 155. Alternatively, left side optical fibers 114 and right side optical fibers 115 may be grouped together and input to a single photodetector 156. Left side optical fibers 114 enter body 133 in a columnar arrangement between first light source 112 and curing tube 126. Right side optical fibers 115 enter body 133 in a columnar arrangement between second light source 113 and curing tube 126. In one example, an optical fiber is provided for each light array in first light source 112 and in second light source 113. Each right side optical fiber 115 is positioned at equal distance between adjacent right side optical fibers 115. Likewise, each left side optical fiber 114 is positioned at equal distance between adjacent left side optical fibers 114.

In one example, third light source 122 and fourth light source 123 are comprised of collimated light sources, laser light for example. The collimated light source may reduce the amount of light that is not directed at a corresponding light receiver such that the signal to noise ratio for detecting an obstructed, partially obstructed, or reduced transmittance curing tube may be improved.

FIG. 1 also shows the locations of cross sections AA, BB, and CC. Cross section AA is shown in FIG. 4, cross section BB is shown in FIG. 3A, cross section CC is shown in FIG. 3B. Cross section AA shows details of the curing tube clarity and/or transmittance system. Cross section BB shows details of a portion of the UV power monitoring system. Cross section CC shows a longitudinal view of a portion of the UV power monitoring system.

Referring to FIG. 2, a schematic of fiber curing system subsystems is shown. Fiber curing system 100 includes a lighting subsystem 200, a coolant subsystem 202, and an inert gas subsystem 204.

Lighting system 200 includes one or more light emitting devices 210 in thermal communication with heat sink 231. In this example, light emitting devices 210 are light emitting diodes (LEDs). Each LED 210 includes an anode 220 and a cathode 222. A switching power source (not shown) supplies 48V DC power to voltage regulator 240 via path or conductor 264. Voltage regulator 240 supplies DC power to the anodes 220 of LEDs 210 via conductor or path 242. Voltage regulator 240 is also electrically coupled to cathodes 222 of LEDs 210 via conductor or path 244. Voltage regulator 240 is shown referenced to ground 260 and may be a buck regulator in one example.

Controller 208 is shown in electrical communication with voltage regulator 240. In other examples, discrete input generating devices (e.g., switches) may replace controller 208, if desired. Controller 208 includes central processing unit (CPU) 290 for executing instructions. Controller 208 also includes inputs and outputs (I/O) 288 for operating voltage regulator 240, for communicating with external controller 228, and for operating other devices. Non-transitory executable instructions may be stored in read only memory 292 while variables may be stored in random access memory 294. Voltage regulator 240 supplies an adjustable voltage and current to LEDs 210. Controller 208 may supply control signals to voltage regulator 240 to adjust voltage regulator output voltage. Controller 208 may also receive input from optical fibers 114 and 115 via photodetectors 155.

A switching device or variable resistor 280 in the form of a field-effect transistor (FET) receives an intensity signal voltage from controller 208 or via another input device. While the present example describes the variable resistor as an FET, one must note that the circuit may employ other forms of variable resistors. By adjusting a control signal to variable resistor 280, controller 208 adjusts current flow through LEDs 210 and the intensity of light produced by LEDs 210.

In this example, at least one element of lighting array 271 includes solid-state light-emitting elements such as light-emitting diodes (LEDs) or laser diodes that produce light. The elements may be configured as a single array on a substrate, multiple arrays on a substrate, several arrays either single or multiple on several substrates connected together, etc. Further, although only a single LED array is shown in FIG. 2, first light source 112 and second light source 113 of FIG. 1 may include one or more light arrays as shown. Each array 271 in the first and second light sources may be supplied power via a single voltage regulator 240 so that all light arrays receive a same amount of power. Alternatively, each light array 271 in the first and second light sources may be supplied power via its own dedicated voltage regulator 240 so that different amounts of electrical power may be provided each light array 271 at the same time. In this way, the amount of electrical power delivered to each light array 271 may be adjusted without adjusting electrical power to other light arrays. Likewise, the lighting intensity of each light array 271 may be adjusted without adjusting the lighting intensity of other light arrays in the fiber curing system 100.

The lighting system circuit shown in FIG. 2 is a closed loop current control circuit. The variable resistor 280 receives an intensity voltage control signal via conductor or path 230 through the drive circuit 222. The variable resistor 280 receives its drive signal from the driver 222. Voltage between variable resistor 280 and array 271 is controlled to a desired voltage as determined by voltage regulator 240. The desired voltage value may be supplied by controller 108 or another device, and voltage regulator 240 controls voltage signal 242 to a level that provides the desired voltage in a current path between array 271 and variable resistor 280. Variable resistor 280 controls current flow from array 271 to current sense resistor 255 in the direction of arrow 245.

The desired voltage may also be adjusted responsive to the type of lighting device, type of work fiber, curing parameters, and various other operating conditions. An electrical current signal may be fed back along conductor or path 236 to controller 208 or another device that adjusts the intensity voltage control signal provided. In particular, if the electrical current signal is different from a desired electrical current, the intensity voltage control signal passed via conductor 230 is increased or decreased to adjust electrical current through array 271. A feedback current signal indicative of electrical current flow through array 271 is directed via conductor 236. The feedback current signal is a voltage level that changes as electrical current flowing through current sense resistor 255 changes.

Additionally, controller 208 may adjust the light intensity control signal in conductor 230 to increase or decrease intensity of light output from array 271 based on light sensed from optical fiber 114 and 115 via photodetector 155. In one example, light intensity of a plurality of arrays 271 is adjusted to a same level by controller 208 in response to input from a plurality of optical fibers 114 and 115 as shown in fiber curing system 100 of FIG. 1. In other examples, light intensity of each array 271 is individually adjusted in response to optical fiber 114/115 receiving light from a selected array 271. For example, in a system as shown in FIG. 1 that includes three light arrays and three optical fibers sensing light emitted from the three arrays, light intensity of a first array is adjusted in response to light sensed via a first optical fiber, light intensity of a second array is adjusted in response to light sensed via a second optical fiber, different than the first optical fiber, and so on.

Controller 208 may also increase the resistance of variable resistor 280 to operate it as a switch and stop current flow through LEDs 210. Further, controller 208 may operate according to the methods of FIGS. 5 and 6 to adjust light intensity output from LEDs 210.

In one example where the voltage between variable resistor 280 and array 271 is adjusted to a constant voltage, current flow through array 271 and variable resistor 280 is adjusted via adjusting the resistance of variable resistor 280. Thus, a voltage signal carried along conductor 244 from the variable resistor 280 does not go to the array 271 in this example. Instead, the voltage feedback between array 271 and variable resistor 280 follows conductor 244 and goes to the voltage regulator 240. The voltage regulator 240 then outputs a voltage signal 242 to the array 271. Consequently, voltage regulator 240 adjusts its output voltage in response to a voltage downstream of array 271, and current flow through array 271 is adjusted via variable resistor 280. Controller 208 may include instructions to adjust a resistance value of variable resistor 280 in response to array current fed back as a voltage via conductor 236. Conductor 244 allows electrical communication between the cathodes 222 of LEDs 210, input 299 (e.g., a drain of an N-channel MOSFET) of variable resistor 280, and voltage feedback input 293 of voltage regulator 240. Thus, the cathodes 222 of LEDs 210 an input side 299 of variable resistor 280 and voltage feedback input 293 are at the same voltage potential.

The variable resistor may take the form of an FET, a bipolar transistor, a digital potentiometer or any electrically controllable, current limiting device. Alternatively, a manually controllable current limiting device may be used as the variable resistor. The drive circuit may take different forms depending upon the variable resistor used.

Heat sink 231 may be air or liquid cooled. In this example, heat sink 231 is liquid cooled via coolant that flows from chiller 249 via coolant pump 264 and coolant flow control valve 265. Controller 208 may adjust the coolant flow rate to heat sink 231 in response to an amount of electrical power supplied to LEDs 210. For example, if the power supplied to LEDs 210 is increased, the coolant flow rate from chiller 249 to heat sink 231 may be increased via increasing coolant pump output and/or coolant valve 265 opening amount. Likewise, if the power supplied to LEDs 210 is decreased, the coolant flow rate from chiller 249 to heat sink 231 may be decreased via decreasing coolant pump output and/or coolant valve 265 opening amount. Alternatively, controller 208 may provide an indication for an external controller to adjust the coolant flow rate.

In this example, inert gas subsystem 204 includes an external controller 228, a gas pump 226, a gas control valve 225, a gas scrubber or filter 224, and a gas storage vessel 223. The locations of gas pump 226, gas control valve 225, filter 224, and gas storage vessel 223 may be rearranged if desired.

Controller 208 may communicate to external controller 228 to increase or decrease an amount of inert gas flowing through curing tube 126. In one example, external controller 228 increases output of gas pump 226 and opens gas valve 225 in response to clarity or transmittance of curing tube 126 decreasing at a rate that is greater than is desired to increase curing tube use life. Alternatively, external controller decreases output of gas pump 226 and closes gas valve 225 in response to clarity or transmittance of curing tube 126 decreasing at a rate that is less than is desired to reduce gas use.

Additionally, controller 208 may communicate the clarity or transmittance degradation rate to external controller 228 so that external controller 228 may adjust the amount of coating applied to fiber 175. The signal to noise ratio of curing tube clarity and/or transmittance provided by collimated light sources 122 and 123 may be sufficient to provide more than degraded/not degraded curing tube clarity and/or transmittance estimates.

Referring now to FIG. 3A, a cross section of light energy sensing ports for a UV power monitoring and control system is shown. FIG. 3A is cross section BB illustrated in FIG. 1.

Body 133 includes a first elliptical reflecting chamber 302 and a second elliptical reflecting chamber 303 for concentrating light emitted from first light source 112 and second light source 113 at fiber 175. First elliptical reflecting chamber 302 has a center location 370. Second elliptical reflecting chamber 303 has a center location 371. LEDs of first light source 112 are positioned along a plane that passes through a first focus of first elliptical reflecting chamber 302, and LEDs direct light in a direction shown by arrow 330. LEDs of second light source 113 are positioned along a plane that passes through a first focus of second elliptical reflecting chamber 303, and LEDs direct light in a direction shown by arrow 331. Light from first light source 112 and second light source 113 converges at 310 which is a second focus for both first elliptical reflecting chamber 302 and second elliptical reflecting chamber 303 as well as the center of body 133. Centers of fiber 175 and curing tube 126 are positioned at 310 such that the lengths of fiber 175 and curing tube 126 are exposed to light for the length of the body 133. Such an arrangement concentrates light from first light source 112 and second light source 113 at fiber 175.

Optical fibers 114 enter body 133 through light sensing ports 320. Optical fibers 115 enter body 133 through light sensing ports 321. Light sensing ports 320 and 321 are positioned between centers 370 and 371 in an area of the periphery of first elliptical reflecting chamber 302 and second elliptical reflecting chamber 303 where light is concentrated and representative of light energy reaching fiber 175. Optical fibers 114 and 115 end or begin flush with first elliptical reflecting chamber 302 and second elliptical reflecting chamber 303.

Third light source 122 and photodetector 360 for determining the clarity or transmittance (the ability of a material to let incoming radiation pass completely through the material) are also shown.

Referring now to FIG. 3B, a cross section of light energy sensing ports for a UV power monitoring and control system is shown. FIG. 3B is cross section CC illustrated in FIG. 1 and the CC cross section runs longitudinally with body 133.

Optical fibers 115 are positioned along the length of body 133 and distances between optical fibers 357 and 358 are substantially equivalent (e.g., ±3.5 mm). Second light source 113 also runs along the length of body 133. A top side of second elliptical reflecting chamber 303 is also shown running the length of body 133.

Referring now to FIG. 4, a cross section of a curing tube clarity and/or transmittance monitoring and control system is shown. FIG. 4 is cross section AA illustrated in FIG. 1. The cross section of FIG. 4 includes many of the elements shown in the cross section of FIG. 3A, and the elements that are the same are labeled with the same numeric identifiers. Therefore, for the sake of brevity a description of already described elements is omitted.

Third light source 122 is positioned offset from the second focus 310 of first elliptical reflecting chamber 302 and second elliptical reflecting chamber 303. By offsetting third light source 122, light from third light source 122 may pass through curing tube 126 without hitting or impinging on fiber 175. Centerline 415 of third light source 122 is shown off set from fiber 175. A similar arrangement applies for fourth light source 123 and fiber 175.

In one example, third light source 122 is a collimated light source such as a laser. Light originates from third light source 122 and it passes through curing tube clarity light port 440 before it reaches curing tube 126. Light that makes it through curing tube 126 may reach receiver or photodetector 360 where a voltage or current proportional to the lights power (e.g., watts/m$^2$) is output from photodetector 360. Light from third light source 122 may pass through curing tube clarity detection port 441 before reaching photodetector 360.

If curing tube 126 is relatively clear, a greater amount of light provided by third light source may be received by photodetector 360. If curing tube 126 is covered or partially covered with matter, a lesser amount of light provided by third light source may be received by photodetector 360. If curing tube 126 blocks more than a desired amount of light from third light source, curing tube 126 may be replaced with a new curing tube.

Thus, the system of FIGS. 1-4 provides for a system for monitoring fiber curing, comprising: an elliptical reflecting chamber including at least two light sensing ports; two light sources, each of the two light sources directed at a curing tube, the curing tube positioned between the two light sources and within at least a portion of the elliptical reflecting chamber; and a light receiver in optical communication with the at least two light sensing ports. The system further comprises a controller including executable instructions stored in non-transitory memory for indicating degradation of the two light sources. The system includes where the light receiver is coupled to the at least two light sensing ports via at least two optical fibers.

In some examples, the system includes where a first of the at least two light sensing ports is positioned between a first of the two light sources and the curing tube, and where the second of the at least two light sensing ports is positioned between a second of the two light sources and the curing tube. The system includes where a first of the two light sources is comprised of a plurality of LED arrays arranged in a first column, and where the second of the two light sources is comprised of a plurality of LED arrays arranged in a second column. The system also includes where the elliptical reflecting chamber further comprises light sensing ports for each LED array in the first and second columns. The system includes where the first column and second column are arranged longitudinally with a long axis of the curing tube. The system further comprises a controller including executable instructions stored in non-transitory memory for indicating a desire to reduce, but not stop, fiber throughput for a fiber UV curing system.

The system of FIGS. 1-4 also provides for a system for monitoring and controlling fiber curing, comprising: a dual elliptical reflecting chamber including a first and a second light sensing ports, the first light sensing port positioned in a first elliptical reflecting chamber of the dual elliptical reflecting chamber, the second light sensing port positioned in a second elliptical reflecting chamber of the dual elliptical reflecting chamber; two light sources, each of the two light sources directed at a curing tube, the curing tube positioned between the two light sources and within at least a portion of the elliptical reflecting chamber; and two light receivers in optical communication with the at least two light sensing ports.

The system includes where the first and second light sensing ports are arranged longitudinally along a length of the curing tube. The system further comprises third, fourth, fifth, and sixth light sensing ports included in the dual elliptical reflecting chamber, the first, third, and fifth light sensing ports arranged longitudinally with a long axis of the curing tube, and the second, fourth, and sixth light sensing ports arranged longitudinally with a long axis of the curing tube. The system includes where the first, third, and fifth light sensing ports are arranged on an opposite side of the curing tube as the second, fourth, and sixth, light sensing ports. The system further comprises a third optical receiver coupled to the third light sensing port, a fourth optical receiver coupled to the fourth light sensing port, a fifth optical receiver coupled to the fifth light sensing port, a sixth optical receiver coupled to the sixth light sensing port. The system further comprises a controller including executable instructions stored in non-transitory memory for adjusting output from the two light sources in response to output from the first, second, third, fourth, fifth, and sixth optical receivers.

Figure 5:
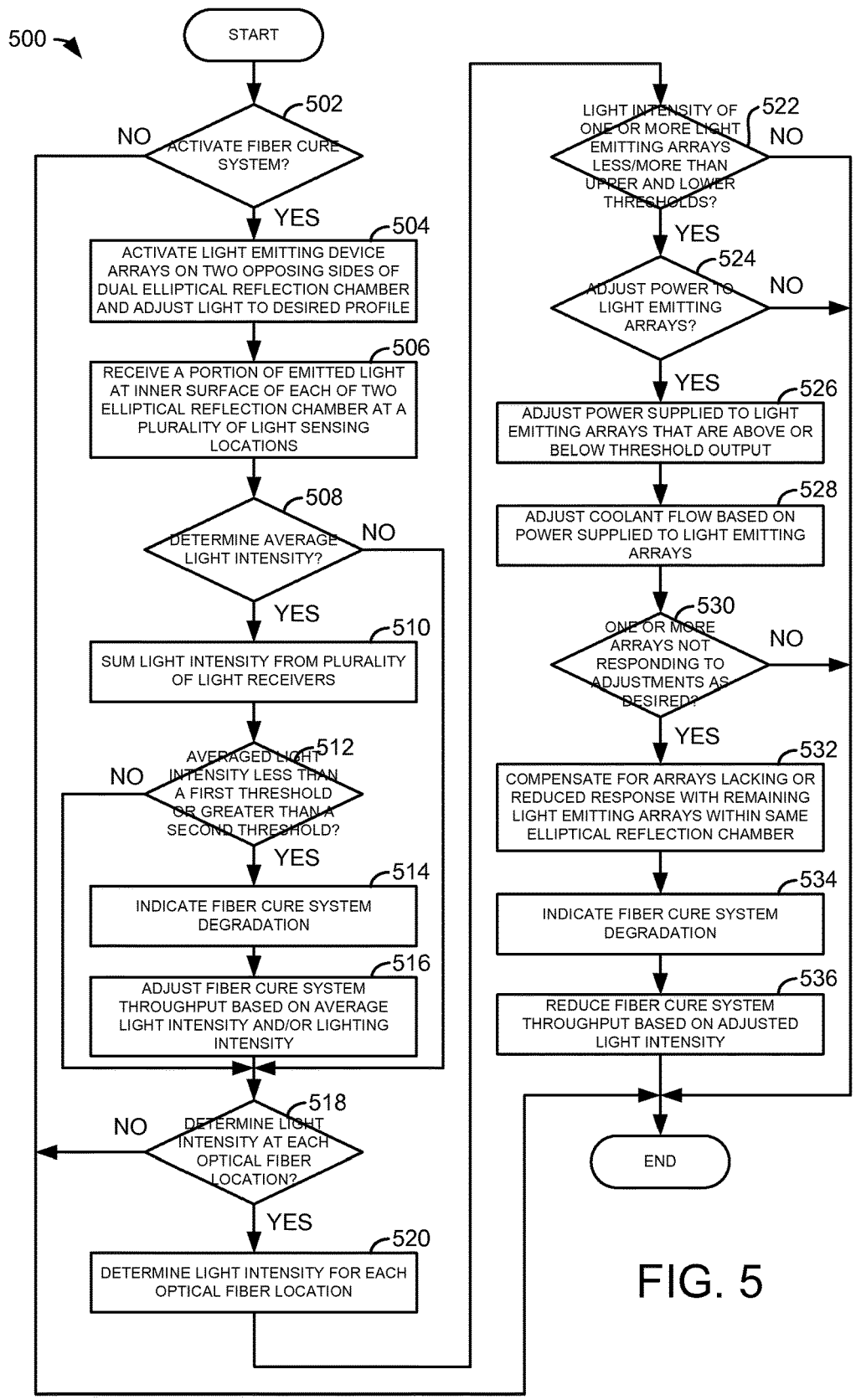
FIG. 5 shows an example method for determining light energy output from a fiber curing system.

Referring now to FIG. 5, a method for determining light energy output from a fiber curing system is shown. The method of FIG. 5 may be stored in non-transitory memory as executable instructions for a controller, such as controller 208 shown in FIG. 2. The method of FIG. 5 may be part of the system shown in FIGS. 1-4.

At 502, method 500 judges whether or not to activate a fiber curing system. The fiber curing system may be activated in response to an operator or controller input. If method 500 judges that the fiber curing system is to be activated, method 500 proceeds to 504. Otherwise, method 500 exits.

At 504, method 500 activates one or more, e.g., two light sources (e.g., 112 and 113 of FIG. 1) on two opposing sides of two elliptical reflecting chambers. In one example, the light sources are comprised of one or more lighting device arrays. The arrays may be supplied electrical energy according to a lighting profile that is based on a position of each lighting array in the respective light sources. In one example, the lighting profile provides an equal amount of electrical energy to each array in the respective light sources. In other examples, each array may be provided a unique amount of electrical power based on an array's position in the light source according to the lighting profile.

For example, a lighting profile may specify that a light source having lighting arrays organized in a single column with three rows, supplies X watts to the lighting array at location (1,1) (e.g, (rows, columns)), X+5 watts to the lighting array at location (2,1), and X+10 watts to the lighting array at location (3,1). Each of the light arrays may be powered by a system as shown in FIG. 2. By adjusting each light array according to a lighting profile it may be possible to affect the curing rate of the fiber's coating along the length of the fiber curing system. Further, by controlling the amount of electrical power provided to each array, it may be possible to compensate for lighting arrays that are outputting more or less energy than is desired by adjusting the power supplied to lighting arrays that are adjacent to degraded lighting arrays or lighting arrays that are receiving more or less electrical power than is desired. Method 500 proceeds to 506 after the two light sources are activated.

At 506, method 500 receives a portion of light emitted by the one or more lighting sources at one or more inner surface of two elliptical reflecting chambers. For example, as shown in FIGS. 3A, 3B, and 4, optical fibers receive light from the inside of first elliptical reflecting chamber 302 and/or second elliptical reflecting chamber 303. The optical fibers may enter the elliptical reflecting chambers at one or more locations between the centers of the two elliptic reflecting chambers as shown in FIGS. 3A and 3B. The optical fibers may all be input to a single photodetector. Alternatively, the optical fibers may each be input to a single photodetector receiving only one optical fiber. Method 500 proceeds to 508 after a portion of the light from the two light sources is received.

At 508, method 500 judges whether or not to determine an average light intensity within the first and second elliptical reflecting chambers. In some examples, it may be desirable to notify an operator or a controller when the average light intensity is less than a threshold light intensity. In other examples, the average light intensity may not be determined to conserve computational time or because it is not presently desired. If method 500 judges to determine the average light intensity within the two elliptical reflection chambers the answer is yes and method 500 proceeds to 510. Otherwise, the answer is no and method 500 proceeds to 518.

At 510, method 500 sums light intensity from a plurality of locations within the two elliptical reflecting chambers. In one example, where optical fibers are bundled together and input to a single photodetector, the photodetector outputs a sum of light energy from each location in the two elliptical reflecting chambers where light is detected. The output from the photodetector may be sampled over a fixed time duration or number of data samples and averaged to determine the average light intensity within the two elliptical reflecting chambers.

In examples where a plurality of optical fibers are individually input to a plurality of photodetectors receiving input from a single optical fiber, the output of each photo detector may be added to the output of all other photodetectors and averaged over time or a number or data samples to determine the average light intensity within the two elliptical reflecting chambers. Method 500 proceeds to 512 after the average light intensity within the two elliptical reflecting chambers is determined.

At 512, method 500 judges whether or not the average light intensity within the two elliptical reflection chambers is less than a first threshold light intensity level or greater than a second threshold light intensity level. The light intensity first and second lighting intensity thresholds may vary depending on fiber coating, ambient temperature, and other conditions. If method 500 judges that the average light intensity within the two elliptical reflection chambers is less than a first light intensity threshold or greater than a second light intensity threshold, the answer is yes and method 500 proceeds to 514. Otherwise, the answer is no and method 500 proceeds to 518.

At 514, method 500 indicates fiber curing system degradation. The indication of degradation may be illuminating a light, sending a message to an external controller that alters fiber processing, or setting a bit in memory. In some examples, a condition of degradation may be indicated more than a single time before action is taken, such as notifying an operator or an external controller. For example, a degraded lighting intensity level may need to be determined three times before indicating degradation. Further, adjustments to electrical power supplied to the lighting arrays may be attempted to bring the average light intensity within the two elliptical reflection chambers to a desired level before degradation is indicated to an operator or an external system.

Method 500 proceeds to 516 after processing the average lighting intensity degradation.

At 516, method 500 adjusts fiber curing system throughput (e.g., a rate fiber is drawn through the fiber curing system) in response to the sensed average light intensity. In one example, a table or function of empirically determined adjustments to a base fiber flow rate through the fiber curing system are stored in memory and indexed based on a difference between a desired average lighting intensity and measured average lighting intensity. For example, if the lighting intensity is Y watts/m$^2$ less than a desired average lighting intensity, the rate fiber moves through the fiber curing system may be reduced by N meters/second. Likewise, if the lighting intensity is Y watts/m$^2$ greater than the desired average lighting intensity, the rate fiber moves though the fiber curing system may be increased so as to reduce waste energy.

Additionally, in one example, current flow through a plurality of light arrays may be increased if the average lighting intensity in the first and second elliptical reflecting chambers is less than a first threshold lighting intensity. Likewise, current flow through the plurality of light arrays may be decreased if the average lighting intensity in the first and second elliptical reflecting chambers is greater than a second threshold lighting intensity. Thus, the lighting intensity may be closed loop controlled to improve the fiber curing system's efficiency. Method 500 proceeds to 518 after adjustments to the fiber curing system are made.

At 518, method 500 judges whether or not to determine lighting intensity at each optical fiber location. In one example, the light intensity where an optical fiber samples light intensity in one of the two elliptical reflection chambers may be indicative of light intensity of a particular lighting array. Thus, output of a specific lighting array may be determined from output of a specific optical fiber sampling a location in one of the two elliptical reflecting chambers.

Method 500 may judge that it is desirable to determining lighting intensity at each optical fiber location in response to the average light intensity determined at 510 or other conditions such as curing system operating time. If method 500 judges to determine lighting intensity at each optical fiber location, the answer is yes and method 500 proceeds to 520. Otherwise, the answer is no and method 500 proceeds to exit.

At 520, method 500 determines lighting intensity output from each optical fiber entering either of two elliptical reflecting chambers. In one example, output from a plurality of photodetectors is converted into a plurality of lighting intensity values having units of watts/m$^2$. The each of the plurality of lighting intensity values corresponds to a lighting intensity at location in one of the two elliptical reflection chambers. Method 500 proceeds to 522 after the lighting intensity at the plurality of locations are determined.

At 522, judges whether or not light intensity at one or more of the plurality of locations in the two elliptical reflecting chambers is less than a first threshold level or greater than a second threshold level. In some examples, first and second threshold levels are provided for each optical fiber that senses light within the two elliptical reflecting chambers. Output from each optical fiber photodetector pair is compare against the first and second threshold levels that correspond to the optical fiber. If output from one or more optical fiber photodetector pairs is less than a first threshold or greater than a second threshold, the answer is yes and method 500 proceeds to 524. Otherwise, the answer is no and method 500 proceeds to exit.

At 524, method 500 judges whether or not to adjust electrical power to the one or more lighting arrays having a lighting intensity that is less than a first level or greater than a second level. In one example, method 500 may adjust electrical power to one or more lighting arrays in response to whether or not the fiber curing system has been activated for a threshold amount of time. If method 500 judges to adjust electrical power supplied to one or more lighting arrays, the answer is yes and method 500 proceeds to 526. Otherwise, the answer is no and method 500 proceeds to exit.

At 526, method 500 adjusts power supplied to lighting arrays that are outputting light with an intensity level that is below a first threshold or above a second threshold. In particular, electrical power supplied to a lighting array that is directs a portion of its light output toward an optical fiber sensing light in an elliptical reflecting chamber may be adjusted when the optical fiber and its associated photodetector senses light intensity less than a first threshold level or greater than a second threshold level. Specifically, if it is determined that a particular lighting array is outputting less than a desired light intensity, current flow to the particular lighting array may be increased to increase light intensity output from the particular lighting array. Electrical power delivered to surrounding light arrays is not adjusted. Similarly, if it is determined that a particular lighting array is outputting greater than a desired light intensity, current flow to the particular lighting array may be decreased to decrease light intensity output from the particular lighting array. Method 500 adjusts electrical power to lighting arrays outputting light intensity above or below a desired lighting range intensity bounded by first and second light intensity threshold and proceeds to 528.

At 528, method 500 adjusts coolant flow to cool lighting arrays. In one example, the coolant flow rate is adjusted in response to the amount of electrical energy added to or reduced from a base amount of electric energy supplied to the lighting arrays of lighting sources being adjusted to compensate for light intensity that is less than or greater than a desired light intensity. For example, if current supplied to a light array reduces electrical power supplied to the light array by 100 watts, the coolant flow to the light source may be reduced by 5%. Likewise, if current supplied to a light array increases electrical power supplied to the light array by 100 watts, the coolant flow to the light source may be increased by 5%. Method 500 proceeds to 530 after coolant flow is adjusted.

At 530, method 500 judges if one or more lighting arrays are not responding to electrical power adjustments as is desired. In particular, light is received by optical fibers as described at 520 and the light intensity is compared to a desired light intensity for each optical fiber after the electrical power adjustments are made at 526. If one or more lighting arrays are not responding to the electrical power adjustments, the answer is yes and method 500 proceeds to 532. Otherwise, the answer is no and method 500 proceeds to exit.

At 532, method 500 attempts to compensate for output of lighting arrays that are not responding to electrical power adjustments as is desired. Note that electrical power adjustments (e.g., adjusting current flow to a lighting array) are used to adjust light intensity output from light arrays. In one example, electrical power is adjusted to lighting arrays that are adjacent or proximate to the lighting array that is not responding as is desired to electrical power. By adjusting electrical power supplied to adjacent lighting arrays, it may be possible to provide a same average lighting intensity as if all lighting arrays are operating as is desired. Therefore, it may be possible to continue to operate the fiber curing system even if one lighting array is not operating as desired. Alternatively, it may be possible to stop applying fiber coating and cure fiber coating that has already been applied before the fiber curing system is stopped to maintain one or more lighting arrays that are not responding as is desired.

For example, if a lighting source includes lighting arrays arranged in three rows and one column (3,1), and the lighting array in the second row directing a portion of its light output toward a second optical fiber position in the first elliptical reflecting chamber, and the second optical fiber and its associated photodetector outputting a light intensity out of a specified range, current supplied to the lighting arrays in the first and second rows may be adjusted while current supplied to lighting array in the second row is maintained at its present level. Noting that light output from the first and third lighting arrays is within a threshold light intensity range as determined from optical fiber and photodetectors receiving a portion of light output from the first and third lighting arrays. The electrical power supplied to the first and third light arrays may be adjusted by varying resistance of variable resistors as described in FIG. 2.

At 534, method 500 outputs an indication of fiber curing system degradation as described at 514. Method 500 proceeds to 536 after fiber curing system degradation is output.

At 536, method 500 reduces the fiber cure system throughput. Since the fiber cure system may be part of a larger fiber manufacturing system, the fiber cure system may send a message to an external controller to reduce the rate fiber flows through the fiber curing system in response to lighting system degradation. In one example, a message to reduce the flow rate of fiber through the fiber cure system is based on a difference between a desired average light intensity in the fiber curing system elliptical reflecting chambers and an actual average light intensity in the fiber curing system elliptical reflecting chambers. For example, if the fiber curing system elliptical reflecting chamber average light intensity is 5% less than is desired, the rate of fiber flowing through the fiber curing system may be reduced by X meters/second. In this way, fiber flowing through the fiber curing system may be exposed to light for long enough for the coating to cure even though lighting intensity within the elliptical reflecting chambers is less than is desired. In some examples, the fiber flow rate may be reduced to zero when the average lighting intensity in the fiber curing system elliptical reflecting chambers is less than a threshold light intensity. Method 500 proceeds to exit after the fiber curing system throughput is adjusted.

Thus, the method of FIG. 5 provides for a method for operating a fiber curing system, comprising: receiving an amount of light energy emitted from two light sources supplying light to a dual elliptical reflecting chamber; and adjusting operation of a fiber curing system in response to the amount of light energy. The method includes where adjusting operation of the fiber curing system includes providing an indication of degradation to a controller or operator. The method further comprises adjusting output of one or more light arrays in one of the two light sources in response to an amount of light energy sensed in one elliptical reflecting chamber of the dual elliptical reflecting chamber. The method also includes where adjusting operation of a fiber curing system includes providing an indication to reduce fiber curing system fiber throughput. The method includes where adjusting operation of a fiber curing system includes providing an indication to adjusted coolant flow to at least one light source. The method includes where adjusting operation of a fiber curing system includes providing adjusting electrical energy supplied to at least one light source.

Figure 6:
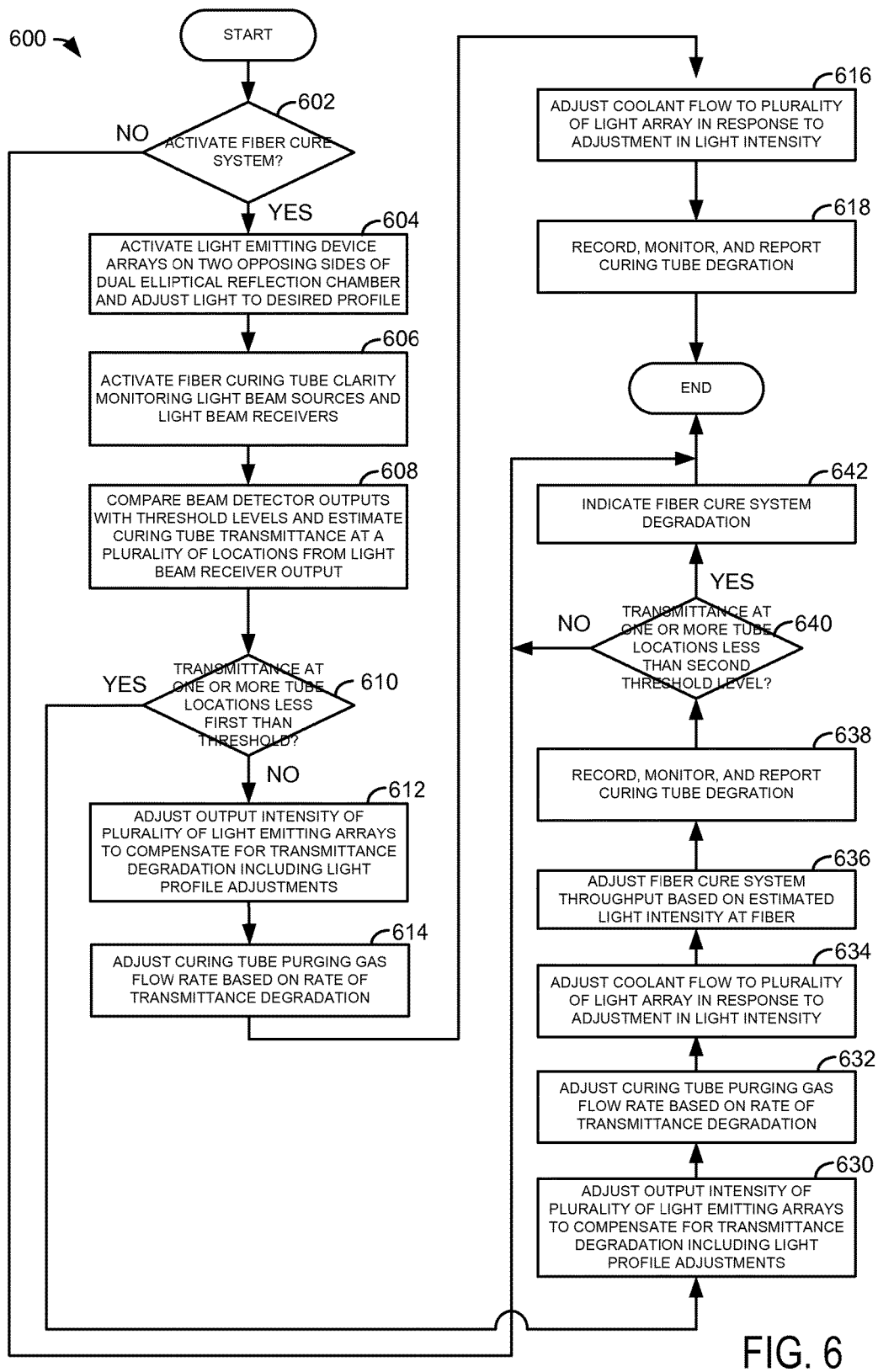
FIG. 6 shows an example method for determining curing tube clarity or transmittance for a fiber curing system.

Referring now to FIG. 6, a method for determining curing tube clarity and/or transmittance for a fiber curing system is shown. The method of FIG. 56 may be stored in non-transitory memory as executable instructions for a controller, such as controller 208 shown in FIG. 2. The method of FIG. 6 may be part of the system shown in FIGS. 1-4.

At 602, method 600 judges whether or not to activate a fiber curing system. The fiber curing system may be activated in response to an operator or controller input. If method 600 judges that the fiber curing system is to be activated, method 600 proceeds to 604. Otherwise, method 600 exits.

At 604, method 600 activates one or more light sources (e.g., 112 and 113 of FIG. 1 on two opposing sides of two elliptical reflecting chambers). In one example, the light sources are comprised of one or more lighting device arrays. The arrays may be supplied electrical energy according to a lighting profile that is based on a position of each lighting array in the respective light sources. In one example, the lighting profile provides an equal amount of electrical energy to each array in the respective light sources. In other examples, each array may be provided a unique amount of electrical power based on an array's position in the light source according to the lighting profile as described in FIG. 5. Method 600 proceeds to 606 after the two light sources are activated.

At 606, method 600 activates the fiber curing tube clarity and/or transmittance light source and light beam receivers. In one example, the fiber curing tube clarity and/or transmittance monitoring and control system activates two light sources and two light beam receivers (e.g., photodetectors). The two light sources and two light beam receivers may be arranged at opposite ends of a curing tube. Method 600 proceeds to 608 after the two light source and two light beam receivers are activated.

At 608, method 600 compares light beam receiver outputs with light beam threshold levels. In one example, the light beam receiver outputs are compared to a table or function of empirically determined curing tube clarity and/or transmittance values that are stored in memory. The table or function outputs a clarity and/or transmittance value for each light beam receiver from 0 to 1 based on output from each light beam receiver. A transmittance value of zero corresponding to no light energy passing through the curing tube from the curing tube clarity light source positioned opposite the curing tube clarity photodetector. A transmittance value of one corresponding to more than a predetermined threshold amount of light energy passing through the curing tube from the curing tube clarity light source positioned opposite the curing tube clarity photodetector. It should also be mentioned that the curing tube light source may be of a different wavelength than the fiber curing light source so that the curing tube clarity photo receiver is not influence by light from the fiber curing light source. In other examples, the curing tube clarity light source may be of the same wave length as the fiber curing light source.

In some examples, the estimated curing tube transmittance for the plurality of curing tube locations may be stored in memory so that a rate of curing tube transmittance degradation may be determined. For example, an estimate of curing tube transmittance at a past time may be subtracted from a curing tube transmittance at the present time and the result may be divided by the difference in time between the past time and the present time to provide a rate of transmittance degradation. Method 600 proceeds to 610 after curing tube clarity and/or transmittance at a plurality of curing tube locations is determined.

At 610, method 600 judges whether or not curing tube clarity or transmittance at the plurality of curing tube locations is less than a first threshold transmittance. The first threshold transmittance may vary with the coating type that is applied to the fiber and/or other curing system conditions. If method 600 judges that curing tube clarity or transmittance is less than a first threshold transmittance level, the answer is yes and method 600 proceeds to 630. Otherwise, the answer is no and method 600 proceeds to 612.

At 612, method 600 adjusts light output intensity of a plurality of light arrays in response to the curing tube clarity or transmittance. By adjusting current supplied to light arrays it may be possible for light intensity to compensate for degradation in curing tube clarity and/or transmittance. For example, if the curing tube transmittance has been reduced by 5%, the light intensity may be increased to compensate for the curing tubes reduced transmittance. In one example, a table or function of empirically determined adjustments to lighting array current are provided so that the lighting array current changes lighting array output light intensity to provide an equivalent amount of light energy at the fiber after the curing tube begins to be covered with matter as before the curing tube begins to be covered with matter. In this way, a substantially equivalent amount of light energy (e.g., the base light energy±5%) may be provided to the fiber for at least a time after matter begins to collect in the curing tube.

Further, when a plurality of lighting arrays are provided electrical current according to a profile that defines a potentially unique amount of current for each light array in the fiber curing system, current amounts in the profile may be adjusted by a curing tube clarity or transmittance modifier so that current supplied to the lighting arrays is provided according to a scaled version of the lighting current profile. It should be noted that light arrays on both sides of the curing tube are adjusted in response to curing tube transmittance.

Additionally, method 600 may compare the desired light intensity, including adjustments for curing tube transmittance, with sensed light as described in FIG. 5. Thus, the light intensity including adjustments for curing tube transmittance may be adjusted in a closed loop manner so that a desired amount of light energy reaches the fiber. Method 600 proceeds to 614 after current supplied to the light arrays is adjusted.

At 614, method 600 communicates with an external controller or adjusts a pump and/or valve to vary flow of an inert gas through the curing tube in response to the curing tube transmittance rate of degradation. In one example, a gas flow adjustment to the inert gas flowing through the curing tube is based on the curing tube's transmittance. The external controller may adjust output of a pump and/or flow control valve to adjust the inert gas flow rate. By adjusting the inert gas flow rate, it may be possible to reduce the rate of curing tube transmittance degradation. If curing tube transmittance is degrading at an expected rate, the inert gas flow rate is maintained at its present flow rate, or the inert gas flow rate may be decreased if the curing tube transmittance is being degraded at a rate that is slower than expected. Method 600 proceeds to 616 after the inert gas flow rate is adjusted.

At 616, method 600 communicates with an external controller or adjusts a pump and/or valve to vary flow of coolant through a lighting array heat sink in response to the lighting array current adjustments provided at 612. In one example, a coolant flow rate adjustment to the heat sink is based on a change in electrical current or power supplied to the lighting arrays. The external controller may adjust output of a pump and/or flow control valve to adjust coolant flow rate. By adjusting the coolant flow rate, it may be possible to maintain the LEDs of the lighting arrays at a desired temperature. Method 600 proceeds to 618 after the coolant flow rate is adjusted.

At 618, method 600 may record curing tube transmittance values, lighting array currents, rate and/or extent of curing tube transmittance degradation, and other control variable to memory. Further, method 600 may report operating conditions and indications of curing tube degradation to an operator or an external controller so that the fiber curing system and other fiber manufacturing systems may take desired actions, such as adjusting fiber flow rate and adjusting an amount of coating applied to the fiber. Method 600 proceeds to exit after fiber curing system conditions are reported and/or stored to memory.

At 630, method 600 adjusts light output intensity of a plurality of light arrays in response to the curing tube clarity or transmittance as described at 612. Method 600 proceeds to 632 after light output intensity is adjusted.

At 632, method 600 communicates with an external controller or adjusts a pump and/or valve to vary flow of an inert gas through the curing tube in response to the curing tube transmittance rate of degradation as described at 614. Method 600 proceeds to 634 after inert gas flow is adjusted.

At 634, method 600 communicates with an external controller or adjusts a pump and/or valve to vary flow of coolant through a lighting array heat sink in response to the lighting array current adjustments provided at 630 as described at 616. Method 600 proceeds to 636 after the coolant flow rate is adjusted.

At 636, method 600 communicates with an external controller or adjusts fiber throughput, or fiber flow rate, through the fiber curing system in response to an estimate of light energy reaching the fiber through the curing tube. In one example, an estimate of light energy at the fiber is based on an amount of light energy output from the lighting arrays and the estimated curing tube transmittance. In one example, the transmittance may be assigned as a number from 0 to 1 as described at 608, and the assigned value is multiplied by a lighting efficiency factor and the light energy emitted from the light arrays to determine an amount of light energy at the fiber. The fiber throughput is adjusted based on the estimate light energy at the fiber. The adjustment to fiber throughput may be empirically determined and stored in a table or function that is indexed by the estimate of light energy at the fiber. Method 600 proceeds to 638 after the fiber throughput is adjusted.

At 638, method 600 may record curing tube transmittance values, lighting array currents, rate and/or extent of curing tube transmittance degradation, and other control variable to memory as described at 618. Method 600 proceeds to 640 after fiber curing system degradation is recorded and/or reported.

At 640, method 600 judges whether or not curing tube transmittance is less than a second predetermined threshold transmittance. If so, the answer is yes and method 600 proceeds to 642. Otherwise, the answer is no and method 600 proceeds to exit.

At 642, method 600 indicates that a high level of curing tube degradation is present. The indication of curing tube degradation may be provided to an external controller so that actions such as adjusting the fiber flow rate may be provided. In some examples, the fiber flow rate may be reduced to zero when the second level of curing tube degradation is determined. Method 600 proceeds to exit after the second level of curing tube degradation is indicated.

It should be mentioned that the methods of FIGS. 5 and 6 may be executed and performed together such that the fiber curing system benefits from both methods. Further, the two methods may exchange information, such as light intensity information for the elliptical reflecting chambers.

As will be appreciated by one of ordinary skill in the art, the methods described in FIGS. 5 and 6 may represent one or more of any number of processing strategies such as event-driven, interrupt-driven, multi-tasking, multi-threading, and the like. As such, various steps or functions illustrated may be performed in the sequence illustrated, in parallel, or in some cases omitted. Likewise, the order of processing is not necessarily required to achieve the objects, features, and advantages described herein, but is provided for ease of illustration and description. Although not explicitly illustrated, one of ordinary skill in the art will recognize that one or more of the illustrated steps or functions may be repeatedly performed depending on the particular strategy being used.

This concludes the description. The reading of it by those skilled in the art would bring to mind many alterations and modifications without departing from the spirit and the scope of the description. For example, lighting sources producing different wavelengths of light may take advantage of the present description.

The invention claimed is:

1. A method for operating a fiber curing system, comprising:
receiving an amount of light energy emitted from one or more light sources of the fiber curing system, the one or more light sources supplying light to a dual elliptical reflecting chamber of the fiber curing system; and
responsive to receiving the amount of light energy, both adjusting operation of the fiber curing system and providing an indication of degradation of the one or more light sources of the fiber curing system to an operator.

2. The method of claim 1, further comprising adjusting output of one or more light arrays in the one or more light sources in response to an amount of light energy sensed in a single elliptical reflecting chamber of the dual elliptical reflecting chamber.

3. The method of claim 1, where adjusting operation of the fiber curing system includes providing an indication to reduce fiber curing system fiber throughput.

4. The method of claim 1, where adjusting operation of the fiber curing system includes providing an indication to adjust coolant flow to at least one of the light sources.

5. The method of claim 1, where adjusting operation of the fiber curing system includes adjusting electrical energy supplied to at least one of the light sources.

6. The method of claim 2, further comprising compensating for output of one or more lighting arrays that are not responding to adjusting.

7. The method of claim 1, further comprising determining an average light intensity within the dual elliptical reflecting chamber based on a sum of light energy output from one or more locations in the dual elliptical reflecting chamber, the sum of light energy output from a photo detector.

8. The method of claim 7, wherein the degradation is determined based on the average light intensity within the dual elliptical reflecting chamber being less than a first threshold or greater than a second threshold.

9. The method of claim 7, wherein adjusting includes increasing current flow through one or more light arrays if the average light intensity within the dual elliptical reflecting chamber is less than a first threshold, and decreasing current flow through the one or more light arrays if the average light intensity within the dual elliptical reflecting chamber is greater than a second threshold.

10. The method of claim 4, where the coolant flow is reduced by 5% if electrical power to the one or more light sources is reduced by 100 watts, and wherein the coolant flow is increased by 5% if the electrical power to the one or more light sources is increased by 100 watts.

11. A method for operating a fiber curing system, comprising:
receiving an amount of light energy emitted from a plurality of light sources of the fiber curing system, the plurality of light sources supplying light to a dual elliptical reflecting chamber of the fiber curing system;
adjusting operation of the fiber curing system in response to the received amount of light energy, where adjusting operation of the fiber curing system includes providing an indication to reduce fiber curing system fiber throughput; and
responsive to determining degradation of the plurality of light sources based on the same received amount of light energy, providing an indication of degradation of the plurality of light sources to an operator.

12. The method of claim 11, further comprising adjusting electrical power to one or more lighting arrays of the plurality of light sources, determining that at least one of the one or more lighting arrays is not responding as desired to the electrical power adjustment, and then further adjusting electrical power to at least one of the one or more lighting arrays proximal to the one or more lighting arrays that did not respond as desired.

13. A method for operating a fiber curing system, comprising:
receiving an amount of light energy emitted from one or more light sources of the fiber curing system via a photo sensor, supplying light to a dual elliptical reflecting chamber of the fiber curing system;
adjusting operation of the fiber curing system in response to the received amount of light energy, where adjusting operation of the fiber curing system includes adjusting a coolant flow rate in response to an amount of electrical energy added to or reduced from a base amount of electric power to the one or more light sources; and
responsive to the same received amount of light energy, providing an indication of degradation of the one or more light sources to an operator,
wherein the one or more light sources and the photo detector are fixed to a body of the fiber curing system, and wherein the body and the dual elliptical reflecting chamber of the fiber curing system are positioned between the one or more light sources and the photo detector.

14. The method of claim 13, where adjusting operation of the fiber curing system includes providing an indication to adjust coolant flow to at least one of the light sources.

* * * * *